United States Patent [19]
Stenglein et al.

[11] Patent Number: 5,952,187
[45] Date of Patent: *Sep. 14, 1999

[54] TOPIRAMATE IMMUNOASSAY

[75] Inventors: Kenneth J. Stenglein, Portland; Daniel B. Cawley, Beaverton, both of Oreg.; Bruce E. Maryanoff, New Hope; Kirk L. Sorgi, Blue Bell, both of Pa.

[73] Assignee: Oxis International, Inc., Portland, Oreg.

[*] Notice: This patent issued on a continued prosecution application filed under 37 CFR 1.53(d), and is subject to the twenty year patent term provisions of 35 U.S.C. 154(a)(2).

[21] Appl. No.: 08/565,143

[22] Filed: Dec. 1, 1995

[51] Int. Cl.$^6$ ............ G01N 33/533; G01N 33/535; C07K 16/44; C12N 9/96
[52] U.S. Cl. ............ 435/7.93; 435/7.5; 435/188; 436/537; 436/545; 436/546; 436/815; 530/388.9; 530/389.8; 530/404
[58] Field of Search ............ 435/7.93, 7.5, 435/188; 436/545, 546, 537, 815; 530/388.9, 404, 389.8

[56] References Cited

U.S. PATENT DOCUMENTS

| | | | |
|---|---|---|---|
| 4,492,762 | 1/1985 | Wang et al. | 436/537 |
| 4,668,640 | 5/1987 | Wang et al. | 436/536 |
| 4,751,190 | 6/1988 | Chiapetta et al. | 436/546 |
| 5,051,361 | 9/1991 | Stenglein et al. | 435/7.9 |

FOREIGN PATENT DOCUMENTS 2111476  6/1983  United Kingdom.

OTHER PUBLICATIONS

J. Burrin et al., Principles and Practice of Immunology, (Price, C.P. and Newman, D. Hrsg.), Stockton Press, NY, pp. 19–52 (1992).

Doose et al., "Comparison of a Fluorescence Polarization Immunoassay with a Capillary GCNPD Assay for the Antiepileptic Agent, Topiramate in Human Plasma," *Epilepsia*, 36, (1995) Supplement 4, p. 48.

Holland et al., "Automated Capillary Gas Chromatographic Assay Using Flame Ionization Detection for the Determination of Topiramate in Plasma," *Journal of Chromatography*, 433 (1988), pp. 276–281.

Maryanoff et al., "Anticonvulsant o–Alkyl Sulfamates. 2,3:4,5–Bis–o–(1–methylethylidene)–β–D–fructopyranose Sulfamate and Related Compounds," *J. Med. Cem.* 30, (1987), pp. 880–887.

Primary Examiner—Mary E. Ceperley
Attorney, Agent, or Firm—Klauber & Jackson

[57] ABSTRACT

The present invention provides a topiramate immunoassay and reagents for use in the immunoassay. In particular, topiramate is derivatized at the sulfamate moiety or the 9-carbon or 10-carbon methyl group of topiramate to add a label bound directly or through a linking group for use as a tracer (competitive analyte analog) or to add a linking group bound to a carrier for use as an immunogen to induce anti-topiramate antibodies. Immunoassay methods and kits are also provided.

37 Claims, No Drawings

TOPIRAMATE IMMUNOASSAY

BACKGROUND OF THE INVENTION

1. Field of the Invention

The present invention relates to immunoassays for topiramate and to topiramate analogs useful as immunogens and tracers and to anti-topiramate antibodies useful in the immunoassays.

2. Description of Related Art

Topiramate (2,3:4,5-bis-O-(1-methylethylidene)-β-D-fructopyranose sulfamate) is a recently developed anti-epileptic drug which has been shown to be useful in the clinical treatment of convulsive disorders. Monitoring blood levels of therapeutic drugs is a routine practice to follow therapy and ensure safety in patients. Quantitation of drugs in tissues or body fluids is also important in pharmacokinetic studies and in monitoring patient compliance. Thus, there is a need for an analytical method to determine the concentration of topiramate in patient samples, particularly plasma and serum.

At present, there are two analytical methods available for measuring topiramate. Both utilize gas chromatography. The first employs gas chromatography coupled with flame ionization detection, the second, gas chromatography with mass spectroscopy. These methods are time consuming, require specialized equipment, highly trained analysts, and extensive sample preparation, and are expensive. The methods also require sample volumes that are too large to be used in pediatric testing unless topiramate concentrations are abnormally high. In short, the existing methods for topiramate are not suitable for routine use in a typical clinical chemistry lab or hospital lab.

Immunoassays have been used for over 20 years for monitoring serum or plasma levels of therapeutic drugs in the clinical laboratory and hospital. Some advantages of immunoassays are that such assays are accurate, sensitive, and in many commercial assay formats, easy to use. An immunoassay to measure topiramate would ensure the availability of an analytical method that could be used routinely to measure drug levels in patient samples. However, it can be difficult or impossible to construct a drug analog suitable for conjugation to a large molecule (such as a protein) to develop an immunogen that induces an antibody that reacts with the drug. Often, the derivatization necessary to create an immunogen sufficiently alters the drug such that the resulting antibodies recognize the analog, but not the drug. Therefore, preparation of analogs that are suitable for conjugation to a protein and induce antibodies that recognize both the analog and the drug is required to develop an immunoassay.

SUMMARY OF THE INVENTION

The present invention provides a topiramate analog that is derivatized to include a linking group. In one embodiment, the topiramate analog is conjugated to a label to form a topiramate analog that acts as a tracer. In another embodiment, the topiramate analog is conjugated to a carrier to form a topiramate analog that acts as an immunogen. In one embodiment, the topiramate analog is of the formula:

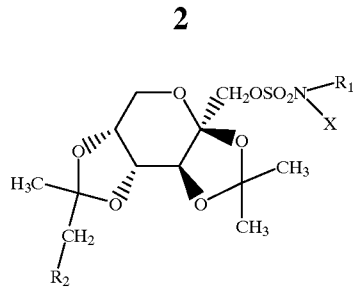

In the formula, one of $R_1$ and $R_2$ is H. The other is R-Y. R is a linking group, and Y is a carrier or a label. When $R_1$ is H, X is H. When $R_1$ is not H, X is H or an alkyl group. In another embodiment, the topiramate analog is of the formula:

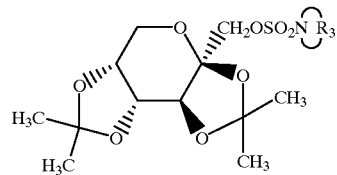

In the formula, $R_3$ is R'-Y. R' is a linking group that includes a heterocyclic group wherein the N of the sulfamate group of topiramate is a member of the ring. Y is a carrier or a label.

The invention also provides anti-topiramate antibodies induced using an immunogen of this invention. A topiramate immunoassay method of this invention is based on competition between topiramate in the sample and a tracer of this invention for anti-topiramate antibodies. In one embodiment, the immunoassay is a fluorescence polarization immunoassay. Immunoassay kits are also provided.

DETAILED DESCRIPTION OF THE INVENTION

The present invention provides novel analogs of topiramate. In one embodiment, the topiramate analog is derivatized to include a linking group to facilitate conjugation to a carrier or a label to form topiramate analogs that can be used as immunogens and tracers, respectively. Topiramate analogs that include a carrier induce antibodies that react with the analog and with topiramate. Topiramate analogs that include a label can be used as a tracer in a competitive immunoassay format. Anti-topiramate antibodies and immunoassays for topiramate using the reagents of this invention are also provided.

Topiramate Analogs

A topiramate analog of this invention is topiramate derivatized to include a chemical moiety that facilitates attachment of a carrier or a label to the topiramate analog. The topiramate analogs of this invention are derivatized at the sulfamate moiety or at the 9-carbon methyl group or at the functionally equivalent 10-carbon methyl group of topiramate. (The structure of topiramate, showing the carbon numbering and the location of the sulfamate moiety, can be found hereinafter in Table 1.) For convenience hereinafter, the discussion of the topiramate 9-carbon group will be understood to also refer to the equivalent 10-carbon position. Derivatizing the sulfamate moiety rather than the 9-carbon methyl group may be advantageous, because the portion of the topiramate analog available for antibody induction and recognition is the region that differs in the topiramate metabolite 9-hydroxy-topiramate (shown in Table 1). Thus, conjugation of a carrier through a linking group via the sulfamate moiety of topiramate produces an immunogen that can elicit antibodies with minimal cross-reactivity with 9-hydroxy-topiramate.

Derivatization of topiramate at the sulfamate moiety or the 9-carbon methyl group provides a topiramate analog that is sufficiently immunologically similar to topiramate that antibodies induced by the analog react with both the analog and with topiramate. Therefore, the topiramate analogs of this invention that include a carrier are capable of inducing anti-topiramate antibodies. In addition, the topiramate analogs can be labeled for use as a tracer in an immunoassay, as described more fully hereinafter.

Two general formulas for topiramate analogs of this invention are shown below.

In the formula, one of $R_1$ and $R_2$ is H. The other is a linking group. When $R_1$ is H, X is H. When $R_1$ is not H, X is H or an alkyl group.

In the formula, $R_3$ is a linking group that includes a heterocyclic group wherein the N of the sulfamate group of topiramate is a member of the ring.

As is well known, drugs or other haptens can be derivatized to include a linking group with a chemical moiety that facilitates attachment of the hapten to a carrier or a label. Linking groups for preparing immunogens and/or tracers from haptens are well known and are described in, for example, U.S. Pat. No. 5,051,361 (issued Sept. 24, 1991 to Stenglein et al.) and in Wong, S., *Chemistry of Protein Conjugation and Cross-Linking*, CRC Press, Inc., Boca Raton, Fla. (1991). Suitable chemical moieties in the linking groups for conjugation include carboxy, amino, imino, amido, carbonyl, nonoxocarbonyl, azido, phosphonium, thio, hydroxy, alkoxy, halo, sulfonyloxy, hydroxyphenyl, imidazolyl, maleimido, as well as other saturated or unsaturated groups. Such linking groups are well known as are various chemistries for synthesizing hapten analogs that bear such linking groups. In some embodiments, the linking group can be reacted with a topiramate precursor so that topiramate (absent one or more hydrogens) is formed attached to the linking group, as described more fully below.

The linking groups can include up to 30 carbon atoms and from 0 to 10 hetero atoms selected from oxygen, sulfur, nitrogen, and halogens. Generally, the linking group is from 1–15 atoms other than hydrogen, more usually, 1–10 atoms other than hydrogen. Longer linking arms can be used when it is desirable to attach the label or carrier at a greater distance from the topiramate molecule.

When X is an alkyl group, the alkyl group usually has from 1–5, more usually 1–3, most usually 1–2 carbons. To produce topiramate analogs wherein X is an alkyl group, conveniently, a topiramate precursor is used. In particular, the acid chloride precursor of topiramate (diisopropylidenefructopyranose chlorosulfate) can be prepared as described in Maryanoff et al., *J. Med. Chem.* 30:880–887 (1987) and reacted with an alkyl-amine to form the N-alkyl-topiramate analog. Briefly, the acid chloride can be prepared as follows. A solution of sulfuryl chloride (93 ml, 1.15 mol) in methylene chloride (100 ml) is added dropwise to a cold solution (−35° C.) of diacetone fructose (150 g, 0.58 mol) in methylene chloride (400 ml) and pyridine (150 ml) to form a reaction mixture. The reaction mixture is stirred and allowed to warm to room temperature. The reaction mixture is stirred for an additional 2 hours. Solvents are removed under vacuum to form the acid chloride topiramate precursor.

The acid chloride precursor can then be reacted with an alkyl-amine to produce a topiramate analog wherein X is an alkyl group. More specifically, the acid chloride precursor can be reacted with an alkylamine such as methylamine, 6-amino caproic acid, N-methyl-glycine, or N-ethyl-glycine, to produce a topiramate analog wherein X is an alkyl group. For example, the acid chloride precursor of topiramate can be reacted with methylamine as described in Maryanoff et al., *J. Med. Chem.* 30:880–887 (1987) to form N-methyl-topiramate. The topiramate acid chloride precursor prepared as described above (35 g, 0.10 mol) is dissolved in anhydrous acetonitrile (150 ml), and methylamine is added. The resulting reaction mixture is tightly stoppered for 3 days, and then the solvent is removed under vacuum. The resulting syrup is subjected to liquid chromatography (dry column of silica gel, ethyl acetate/hexane, 4:1) to yield a light yellow syrup (4.1 g, 12%) which is homogeneous by thin layer chromatography and NMR. Similar methods can be used with other alkyl amines to form other N-alkyl topiramate analogs.

The linking group can include a heterocyclic group wherein the N of the sulfamate group of topiramate is a member of the ring. A heterocyclic group is a closed ring structure, usually of either five or six members, in which one or more atoms in the ring is an element other than carbon. A suitable exemplary heterocyclic group is, for example, pyrrolidine, piperidine, piperazine, or morpholine.

To form the heterocyclic group, generally a topiramate precursor is used. In particular, the acid chloride precursor of topiramate can be reacted with a heterocycle to form a heterocyclic topiramate analog.

The topiramate analog linking group can include a leaving group. The leaving group is a chemical moiety that is active in conjugating the topiramate analog to a label or a carrier. As part of the conjugation process, one or more atoms of the leaving group are given up. Furthermore, conjugation of a label or a carrier generally results in modifying the leaving group so that the linking group in the conjugate includes the residue following such modifications. For convenience herein, the term "linking group" will refer to the linking group attached to topiramate to form a topiramate analog and to the residue of the linking group following conjugation to a label or a carrier.

In several embodiments exemplified herein, topiramate is derivatized with a linking group that includes a carboxyl group that is used to attach the analogs to a label or a carrier. In an exemplary conjugation process, the carboxyl group on the topiramate analog is reacted with N-hydroxysuccinimide (NHS) to form an active ester. This active ester reacts with amino groups to form topiramate analog conjugates. The amino groups can be present in small molecules such as fluorescein or biotin derivatives or in macromolecules such as proteins such as bovine serum albumin or peroxidase. When the conjugate contains a carrier or a label, the topiramate analog can be used as an immunogen or as a tracer, respectively.

Although the topiramate analogs described herein are exemplified with a carboxyl group that participates in the conjugation process, other chemical moieties that can participate in conjugation are well known and are also suitable. For example, amine derivatives or thiol derivatives of topiramate can be coupled to carriers or labels using methods well known to those of skill in the art. Exemplary topiramate analogs are listed below in Table 1, followed by the structures for these compounds. Compound No. 5, 9-hydroxy-topiramate, is a known topiramate metabolite.

TABLE 1

TOPIRAMATE AND ITS ANALOGS 1. 2,3:4,5-bis-O-(1-methylethylidene)-β-D-fructopyranose sulfamate (Topiramate)

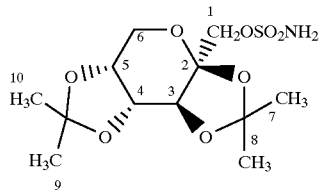

2. N-carboxymethyl-topiramate, sodium salt monohydrate (also referred to as topiramate glycine analog or TGA)

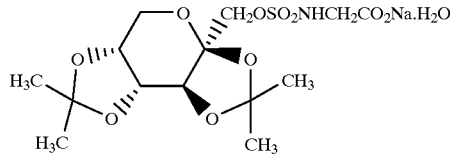

3. N-(5-carboxypentyl)-topiramate, sodium salt (also referred to as topiramate caproic acid analog, sodium salt or TCA)

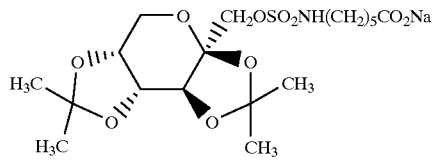

4. 9-carboxymethyl-topiramate (also referred to as topiramate levulinic acid ketal analog or 9-CMT)

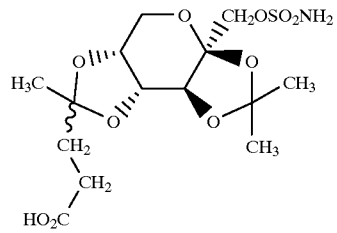

TABLE 1-continued

TOPIRAMATE AND ITS ANALOGS 5. 9-hydroxy-topiramate (9-OH-T)

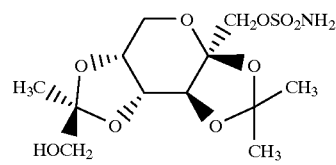

The topiramate analogs of this invention were prepared using standard chemical synthesis methods.

Exemplary methods to produce analogs 2–4 are described in detail in Examples 1–3. Preparation of topiramate and of several topiramate analogs that can be used as starting materials is described in Maryanoff et al., *J. Med. Chem.* 30:880–887 (1987). In addition, topiramate is sold under the tradename TOPAMAX by Ortho/McNeil Pharmaceuticals.

The topiramate analogs of this invention also include topiramate bound to a carrier or to a label to form an immunogen or a tracer, respectively. In the immunogens of this invention, a topiramate analog that includes a linking group is conjugated to a carrier. In the tracers of this invention, a topiramate analog that includes a linking group is conjugated to a label. These topiramate analogs can be represented by the two general formulas shown below.

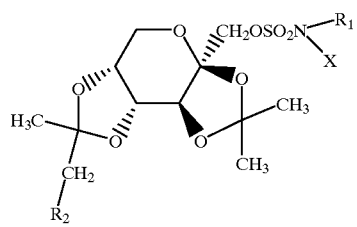

In the formula, one of $R_1$ and $R_2$ is H. The other is R-Y. R is a linking group, and Y is a carrier or a label. When $R_1$ is H, X is H. When $R_1$ is not H, X is H or an alkyl group.

In another embodiment, the topiramate analog is of the formula:

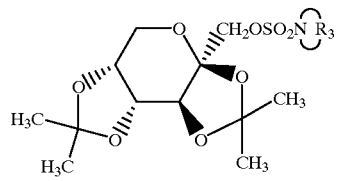

In the formula, $R_3$ is R'-Y. $R_1$ is a linking group that includes a heterocyclic ring group wherein the N of the sulfamate group of topiramate is a member of the ring. Y is a carrier or a label.

An immunogen of this invention is a topiramate analog that includes a carrier. The term "carrier" is used herein as in the art to indicate a substance that is immunogenic in a selected host animal. Preparation of immunogens by linking a hapten to a carrier is well known. Selection of the carrier and administration route varies, depending on the host animal. Carriers are generally large molecules, usually polymers, most usually large proteins from a species other than that of the host animal. Bovine serum albumin (BSA) and keyhole limpet hemocyanin (KLH) are frequently used as carriers for inducing antibodies in mice, rats, goats, rabbits, chickens, and sheep. Exemplary preparations of immunogenic topiramate analogs for inducing anti-topiramate antibodies are described in the examples. In those exemplary immunogen preparations, R-Y is $(CH_2)_nCO$—NH— (carrier), where n is from 1 to 9. More specifically, there are examples wherein n is 1 or 5, and BSA is the exemplary carrier.

The term "tracer" is used herein as in the art to refer to a labeled analyte analog used in a competitive immunoassay format. A tracer of this invention is a topiramate analog that includes a label which is attached to topiramate through a linking group. The term "label" is used to refer to substances that can be detected directly or indirectly. Labels that can be detected directly include, for example, a radionuclide or a fluorochrome. Labels can also be detected indirectly through one or more reactions. Such labels include enzymes that are detected by production of a colored product. Such enzyme labels and their color development systems are well known. Other such labels include use of a member of a specific binding pair such as biotin/avidin. Labels suitable for use in immunoassay procedures are well known and include, for example, enzymes, radionuclides, fluorochromes, biotin, and the like. Conveniently, the label is a fluorochrome.

Suitable fluorochromes include rhodamine (e.g., tetramethylrhodamine isothiocyanate—TRITC), phycoerythrin (PE), allophycocyanin (APC), Texas Red (Molecular Probes, Eugene, Oreg.), and preferably fluorescein. Although allophycocyanin and phycoerythrin are suitable fluorochromes, they cannot be used for fluorescence polarization immunoassays, because they are too large. Suitable fluoresceins include fluorescein isothiocyanate (FITC), (2-aminoethyl)-thioureido-fluorescein (FTED), fluorescein-thiosemicarbazide (FTSC), (2-aminoethyl)-ureido-fluorescein (FAMCO-E), erythrocin (tetra-iodo-fluorescein), and fluoresceinamine (FAM).

The fluorochrome can be joined to the linking group through any available position on the fluorochrome nucleus. Fluorescein labels consisting of the linking group attached to the 5-, 6-, 4'- and 5'-positions are preferred. Labels attached through the 5- and/or 6-position are most preferred. (See, for example, Table 2, tracers 4–10.)

For convenience, tracers having a fluorescein residue attached to the linking group through the 5-position of the fluorescein moiety are designated isomer I. Tracers having a fluorescein residue attached to the linking group through the 6-position of fluorescein are designated isomer II. Unless otherwise specified, no distinction will be made between isomers, or a mixture of isomers. For fluorescein and rhodamine-labeled tracers, little or none of the lactone form exists during fluorescence measurements and the carboxylated forms exist primarily as salts. The fluorochrome can be a homogeneous composition or a mixture of isomers. In addition, the fluorochrome can be used in its lactone form or as a biologically acceptable salt (e.g., Na, K, ammonium and similar salts) so that the fluorochrome can exist in its ionized state in the immunoassay.

Table 2 below, lists topiramate analog immunogens and tracers that were prepared as described in the Examples: these were derived from exemplary topiramate analogs listed in Table 1. In the preparation of immunogens and tracers, topiramate analogs of Table 1 were activated by standard procedures to form the N-hydroxysuccinimide ester of the carboxylic acid group. The active ester in turn reacted with a primary amine in the carrier or the label to form an amide.

Alternatively, carboxylic acids can be condensed with amines using other methods known in the art. Synthesis methods for formation of the amides of carboxylic acids are well known and are described in, for example, U.S. Pat. No. 5,051,361 (to Stenglein et al., issued Sep. 24, 1991). Methods of making immunogenic conjugates are also described in *Methods in Immunology and Immunochemistry*, (Curtis A. Williams and Merrill W. Chase eds., Volume 1, 1967). Those references are incorporated by reference herein in their entireties. In addition, exemplary methods to produce exemplary topiramate analogs useful as tracers or as immunogens are described in detail in the Examples. The exemplary topiramate analogs useful as immunogens and tracers are listed below in Table 2 and followed by the structures for these compounds.

TABLE 2

TOPIRAMATE CONJUGATES

1. TGA:BSA

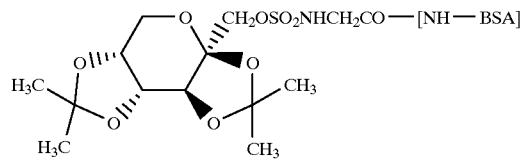

2. 9-CMT:BSA

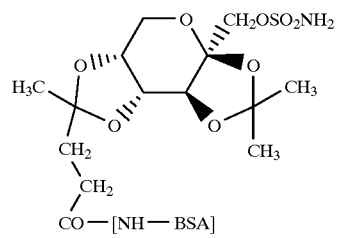

TABLE 2-continued
TOPIRAMATE CONJUGATES
3. TCA:BSA
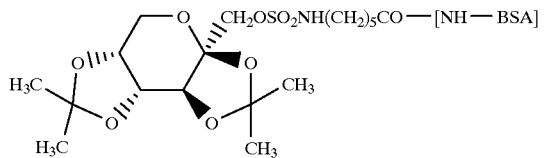
4. TGA:FTED
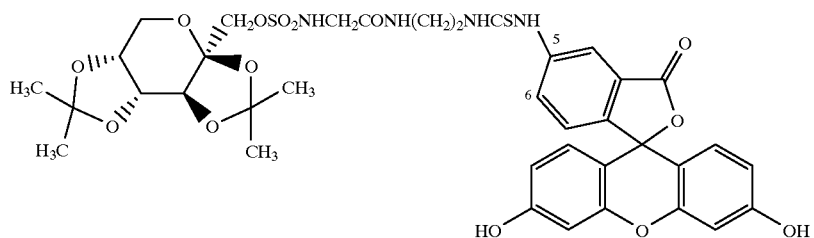
5. TGA:FTSC
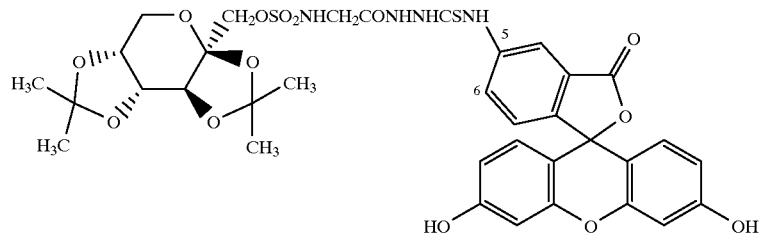
6. TGA:FAMCO-E
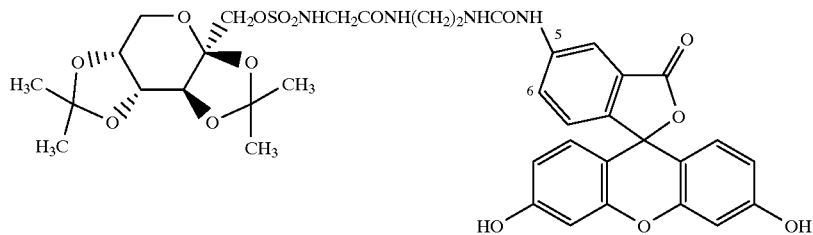
7. TGA:Gly-FAM
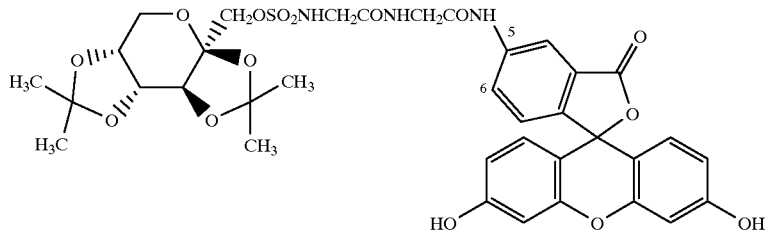
8. TCA:FTED TABLE 2-continued
TOPIRAMATE CONJUGATES
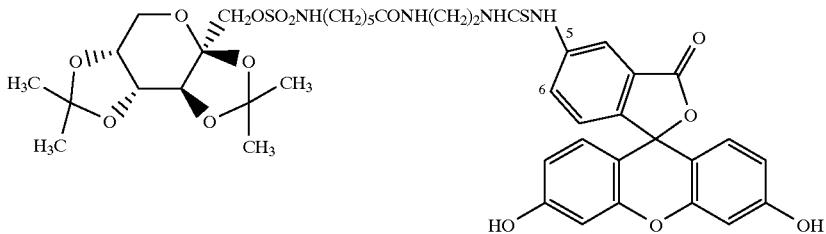
9. TCA:FAMCO-E
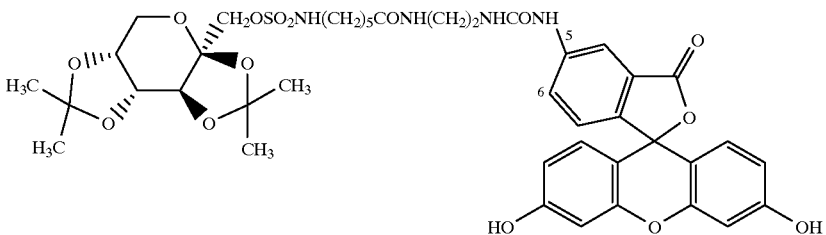
10. TCA:FAMCO-E tracer, isomer II
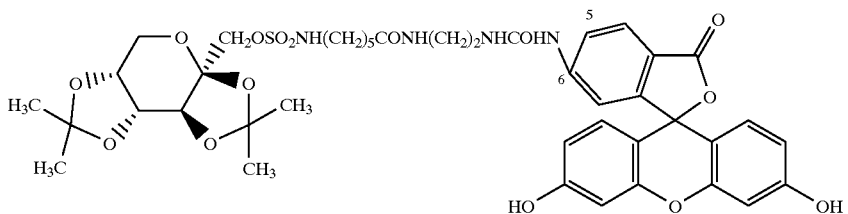
11. 9-CMT:FAMCO-E
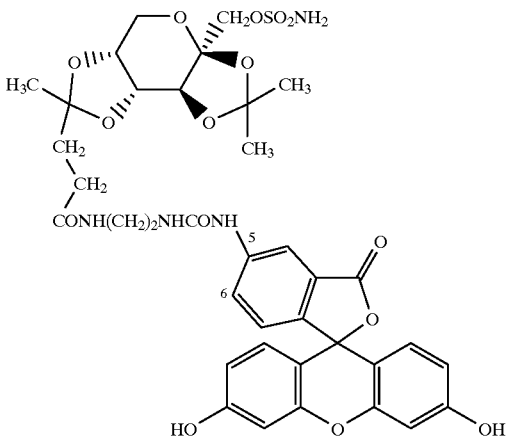
12. TGA-R:biotin

TABLE 2-continued

TOPIRAMATE CONJUGATES

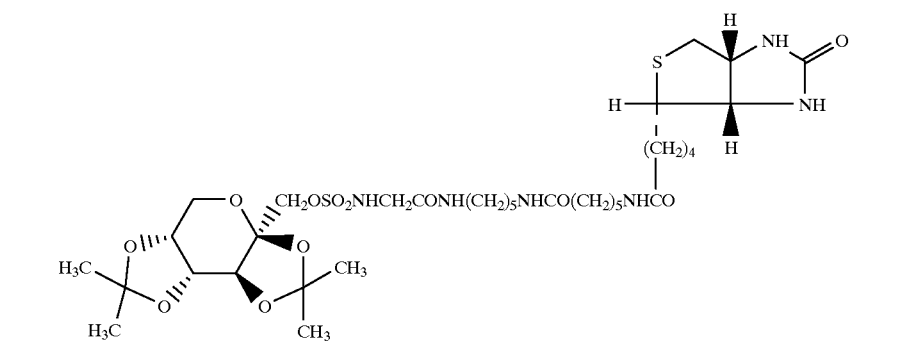

Anti-Topiramate Antibodies

Anti-topiramate antibodies of this invention react with topiramate and with the topiramate analog used to induce the antibodies. Anti-topiramate antibodies can be induced using an immunogen of this invention formulated in an aqueous solution such as water, normal saline, phosphate buffered saline, and the like or provided in an adjuvant or similar composition. The induced antibodies can be tested to determine whether the composition is specific for topiramate.

If a polyclonal anti-topiramate antibody composition does not provide the desired specificity (e.g., has unacceptable levels of crossreactivity with topiramate metabolites for samples with high levels of metabolites), the antibodies can be used to assay samples with low levels of metabolites or be used in procedures where crossreactivity with metabolites is not a concern, as described more fully below.

Monoclonal anti-topiramate antibodies can also be prepared by conventional methods. A mouse can be injected with a composition containing an immunogen of this invention and spleen cells obtained. Those spleen cells can be fused with a fusion partner to prepare hybridomas. Antibodies secreted by the hybridomas can be screened to select a hybridoma wherein the antibodies react with topiramate. Conveniently, antibodies can be screened to exhibit minimal reaction with topiramate metabolites, such as 9-hydroxy-topiramate. Hybridomas that produce antibodies of the desired specificity are cultured by standard techniques. Hybridoma preparation techniques and culture methods are well known and constitute no part of the present invention.

Exemplary preparations of monoclonal and polyclonal anti-topiramate antibodies are described in the examples. It is noted that, in most patient samples, a single topiramate metabolite is present at a small fraction (usually less than 4% percent) of the concentration of topiramate in the sample. However, several metabolites can exist and in aggregate can represent up to 20% of the drug dose in normal patients and up to 50% on occasion in patients with increased metabolism or medical problems such as renal failure, for an example.

Although crossreactivity of anti-topiramate antibodies with the metabolite is of little consequence in obtaining an accurate immunoassay value in samples with small amounts of topiramate metabolites, preferably, the anti-topiramate antibodies do not substantially crossreact with topiramate metabolites. By "not substantially crossreact" is meant that when the antibodies are used in a competitive immunoassay format, at least about 5-fold more 9-hydroxy-topiramate is required to achieve the same amount of antibody inhibition as topiramate.

Immunoassays

Numerous quantitative immunoassay formats for detecting a hapten such as a drug or other small molecule in a body fluid are known. An assay method for topiramate has the following elements. The method includes combining the sample with an anti-topiramate antibody and detecting the amount of the anti-topiramate antibody-topiramate complex as indicative of the amount of topiramate in the sample. The particular manner in which topiramate is detected is not significant for the purpose of this invention so long as the method provides the desired degree of sensitivity and reliability. Various methods for performing immunoassays are described in Tijssen, P., *Practice and Theory of Enzyme Immunoassays*, (R. H. Burdon and P. H. van Kniffenberg eds., Volume 15, 1985); and *The Immunoassay Handbook*, (David Wild ed., 1994).

The sample for a topiramate immunoassay is a body fluid, generally blood, more specifically serum or plasma. However, use of other body fluids such as urine or saliva is also contemplated.

A number of different types of immunoassays are well known using a variety of protocols and labels. The assay conditions and reagents can be any of a variety found in the prior art. The assay may be heterogeneous or homogeneous, and conveniently a competitive assay. As indicated by the induction of antibodies that recognize topiramate analogs derivatized at either the sulfamate moiety of topiramate or at the 9-carbon methyl group of topiramate, topiramate has at least two different epitopes that are capable of antibody recognition. However, as with other small molecules, when one antibody binds to topiramate or a topiramate analog, recognition of topiramate by a second antibody is blocked, precluding use of conventional sandwich type immunoassays wherein two antibodies bind to two epitopes on the analyte.

A topiramate immunoassay employs anti-topiramate antibodies that can be polyclonal or monoclonal. Conveniently, the assay can be based on competition, where topiramate in the sample competes with a fixed amount of a topiramate tracer of this invention. The amount of tracer required for any competitive assay varies depending on a number of well known factors. For example, when the tracer is labeled with a fluorochrome, the amount of tracer required for an assay is empirically determined. The amount of tracer used must provide an appropriate signal for the detector used in relation to the background signal and must provide an amount of tracer so that the affinity of the anti-topiramate antibodies for the tracer and for the range of topiramate that may be present in the sample provide the desired sensitivity.

In competitive immunoassays, the antibody preparation used is induced by an immunogen that includes a topiramate analog derivatized at the same position as the topiramate analog used as the tracer. That is, the immunogen used to induce the antibody composition and the tracer both include topiramate analog derivatized at either the sulfamate moiety or 9-carbon methyl group of topiramate.

Binding between the antibodies and topiramate in the sample can be determined in a number of ways. For example, any topiramate present in the sample can compete with a predetermined, fixed amount of labeled topiramate analog (tracer) for anti-topiramate antibody binding sites. The amount of tracer affixed to the solid phase or remaining in solution can be determined. In one embodiment, a tracer labeled with biotin is affixed to the solid phase by binding to solid phase-affixed avidin. Topiramate in the sample competes with solid phase-affixed topiramate tracer for anti-topiramate antibodies. Labeled anti-topiramate antibodies affixed to the solid phase or remaining in solution can be detected. The anti-topiramate antibodies can be labeled directly or detected using labeled second antibody specific for the species of the anti-topiramate antibodies.

Numerous other formats can be used. For example, anti-topiramate antibodies can be solid phase affixed. A fixed amount of topiramate tracer can compete with topiramate in the sample for antibody binding. The amount of solid phase-affixed tracer or tracer remaining in solution is determined. The tracer can have a label that is detected directly as with a radionuclide, a fluorochrome, or the like, or indirectly as with an enzyme. Alternatively, the topiramate tracer can be labeled with biotin and detected with enzyme-labeled avidin or avidin-labeled antibodies. Those avidin-labeled antibodies can be labeled directly or detected with labeled second antibody.

In another embodiment, the immunoassay is a fluorescence polarization immunoassay that measures topiramate in patient samples. Conveniently, the fluorescence polarization immunoassay can be used in an automated system such as the TDx® and TDxFlx® analyzers (commercially available from Abbott Laboratories), designed for drug monitoring in the clinical chemistry laboratory and hospital.

A fluorescence polarization immunoassay uses a fluorescently labeled tracer having a small molecular weight (typically less than 5000). The tracer is placed in an incident beam of plane-polarized light. The light is absorbed and can be reemitted as fluorescence. Because of the rapid Brownian motion of small molecules, the emitted fluorescence is depolarized. A large increase in the size of the tracer greatly increases its rotation time, resulting in the emitted fluorescent light remaining polarized. The binding of antibodies to a fluorescein-labeled tracer thus causes polarization of the emitted light. Analyte in the sample competes with tracer for antibody binding, and thus increases the depolarization of the fluorescence. The extent of depolarization is dependent on the concentration of the analyte in the sample. Thus, a standard curve for a competitive immunoassay wherein the amount of depolarization of fluorescence correlates with increasing analyte concentration can be prepared.

Reagents for assaying topiramate can be conveniently packaged in kits. An immunoassay kit for assaying topiramate can include an anti-topiramate antibody and a topiramate analog tracer of this invention.

This invention is further illustrated by the following specific but non-limiting examples.

Temperatures are given in degrees Centigrade and concentrations as weight percent unless otherwise specified. Procedures which are constructively reduced to practice are described in the present tense, and procedures which have been carried out in the laboratory are set forth in the past tense. All citations in the above specification and the following examples are incorporated herein by reference in their entireties.

EXAMPLE 1

Preparation of N-Carboxymethyl-Topiramate

In an exemplary procedure, N-carboxymethyl-topiramate (topiramate glycine analog or TGA) was prepared as described below from topiramate (Maryanoff et al., *J. Med. Chem.* 30:880–887 (1987).

33.9 g (0.1 mol) of topiramate, 16.1 g (0.1 mol) of hexamethyldisilazane, and about 1 ml of chlorotrimethylsilane was added to 150 ml of tetrahydrofuran to form a solution. The solution was refluxed for 5 hours and cooled to room temperature. with stirring, 3.0 g (0.1 mol) of 80% NaH was added portion-wise over about a 10 minute period to form a reaction mixture. The reaction mixture became very thick and 20 ml of dimethylformamide and 100 ml of tetrahydrofuran were added to dissolve the precipitate in the reaction mixture, and the reaction mixture became a homogenous solution. Then, 19.5 g (0.1 mol) of tertiary-butyl-bromoacetate was added dropwise over 30 minutes to the reaction mixture. The reaction mixture was stirred overnight. The reaction mixture was diluted with 500 ml of ethyl acetate and washed with water (2×100 ml), then saturated brine solution (saturated NaCl in water) (100 ml), dried (using $MgSO_4$), and the solvent was removed in vacuo to afford crude tertiary-butyl glycinate analog, as a sticky white solid. The crude solid containing tertiary-butyl glycinate analog was chromatographed on silica gel using 18% ethyl acetate/hexane (v/v) as the eluent to produce 17.2 g (38% yield) of the tertiary-butyl glycinate analog as a white solid.

Approximately 9.0 g (19.9 mmol) of the tertiary-butyl glycinate analog was added portion-wise to 90 ml of trifluoroacetic acid, while stirring at room temperature to form a reaction mixture. After 10 minutes, the reaction mixture was filtered to remove a small amount of undissolved material, and the solvent was removed in vacuo to afford the crude glycine analog as a thick oil. The oil was dissolved in 150 ml of 1 N NaOH and washed with diethyl ether (2×50 ml). The aqueous layer was acidified to pH 3 using 3 N HCl and extracted with methylene chloride (3×100 ml). The combined organic extracts were concentrated in vacuo to yield 6.68 g (84% yield) of the glycine analog as a white foam.

The glycine analog (6.0 g, 15.1 mmol) was dissolved in 13.6 ml of 1.0 N NaOH. The water was removed in vacuo, and the resultant residue was azeotropically dried using toluene to yield the crude sodium glycinate 4 as a white solid. The white solid was triturated with diethyl ether (2×50 ml), and the resultant solid isolated by vacuum filtration to produce 5.3 g (80% yield) of the sodium glycinate hydrate (N-carboxymethyl-topiramate). The melting point of the N-carboxymethyl-topiramate was 169.0 to 170.0° C. The elemental analysis calculated for N-carboxymethyl-topiramate ($C_{14}H_{22}NO_{10}SNa \cdot H_2O$) is C, 38.44; H, 5.53; N, 3.20; S, 5.26; and Na, 5.26. The elemental analysis determined for the N-carboxymethyl-topiramate analog was C, 38.27; H, 5.59; N, 3.08; S, 5.50; Na, 5.50. % $H_2O$ (KF); 4.12%. (KF indicates that the water content was determined using the Karl Fischer method and is reported as % w/w).

N-carboxymethyl-topiramate (TGA) was obtained as the sodium salt, monohydrate, to prepare immunogens, tracers, and biotin-conjugates in the following examples.

EXAMPLE 2

Preparation of N-(5-Carboxypentyl)-Topiramate (TCA)

In an exemplary procedure, N-(5-carboxypentyl)-topiramate (topiramate caproic acid analog or TCA) was prepared from 2,3:4,5-bis-O-(1-methylethylidine)-chlorosulfate (Maryanoff et al., *J. Med. Chem.* 30:880–887 (1987)) as described below.

A solution of 2,3:4,5-bis-O-(1-methylethylidine)-chlorosulfate (35.8 g, 0.10 mol) in methanol (200 ml) was added dropwise to a solution of 6-aminocaproic acid (26.2 g, 0.20 mol) and pyridine (7.91 g, 0.10 mol) in methanol (300 ml) slowly over a 2.25-hour period to form a mixture. The mixture was heated at reflux for 2.5 hours, then concentrated under reduced pressure to give a red-orange oil. The oil was dissolved in distilled water (300 ml) and ethyl acetate (200 ml), then basified with a 4 M NaOH solution to pH 10–12. The layers were separated, and the aqueous layer was repeatedly extracted with ethyl acetate (12×200 ml) until the by-product, diacetone fructose, was removed. The aqueous layer was then acidified with concentrated HCl to pH 5.0 and extracted with ethyl acetate (4×150 ml). The organic extracts were combined, dried ($MgSO_4$), filtered, and concentrated to give the caproic acid derivative as an oil in 19.5% crude yield.

The oil was dissolved in 2-propanol (230 ml) and treated with a 4 M NaOH solution (13 ml) to form a reaction mixture. The reaction mixture was concentrated, and the resulting solid slurried overnight at room temperature in ISOPAR E (a high boiling hydrocarbon commercially available from EXXON Corporation. The slurry was filtered, and the recovered solid was washed with ISOPAR E. Air drying produced 23.64 g (97.5% yield) of the sodium caproate analog (N-(5-carboxypentyl)-topiramate) as a white solid having a melting point of 197.0–202.0° C. The elemental analysis calculated for $C_{18}H_{30}NO_{10}SNa$ is C, 45.47; H, 6.36; N, 2.95; S. 6.74; Na, 4.83. The elemental analysis determined for the analog was C, 44.87; H, 6.31; N, 2.89; S, 6.44; Na, 5.08.

N-(5-carboxypentyl)-topiramate (TCA) was used as the sodium salt to prepare immunogens and tracers in the following examples.

EXAMPLE 3

Preparation of 9-Carboxymethyl-Topiramate (9-CMT)

In an exemplary procedure, 9-carboxymethyl-topiramate (9-CMT) (the levulinic acid ketal analog) was prepared as described below.

Triethyl orthoformate (24.6 g, 0.166 mol) was added to a stirred solution containing 24.0 g (0.166 mol) of ethyl levulinate, 0.8 ml of sulfuric acid and 300 ml of absolute ethanol to form a reaction mixture. After stirring the reaction mixture for 30 minutes at room temperature, 16.4 g (0.055 mol) of 2,3-O-(1-methylethylidine)-B-D-fructopyranose sulfamate (Maryanoff et al., *J. Med. Chem.* 30:880–887 (1987) was added and the stirring was continued for 16–18 hours. Solid sodium carbonate (80.0 g, 0.75 mol) was added to the reaction mixture followed by distilled water (100 ml) to form a reaction mixture having a pH of 7.0. The reaction mixture was filtered and diluted with ethyl acetate (about 500 ml. The layers were separated, and the organic layer was washed with a saturated sodium chloride solution (3×200 ml), dried over sodium sulfate, filtered, and concentrated to afford an oil as a mixture of ketal, a small amount of diol, and ethyl levulinate. The oil was repeatedly triturated with hexane until the excess ethyl levulinate was removed, and then the oil was dissolved in 125 ml of methanol to form a methanol solution. 1 N NaOH (250–300 ml) was added to the methanol solution, and the resulting reaction mixture was heated at reflux for approximately 2 hours. After cooling to room temperature, the reaction mixture was extracted with ethyl acetate (3×100 ml). The aqueous layer was acidified to pH 4.0 using 3 N HCl and extracted with ethyl acetate (3×100 ml). The organic extracts were combined, dried (MgSO4) overnight, filtered, and concentrated to give 15.7 g (71.8% yield) of the levulinic acid ketal derivative (9-carboxymethyl-topiramate) as a white brittle foam having a melting point of 42.0–45.0° C. The elemental analysis calculated for $C_{14}H_{23}NO_{10}S$ was C, 42.31; H, 5.83; N, 3.52; S, 8.07. The elemental analysis determined was C, 42.55; H, 5.83; N, 3.38; S, 7.57.

9-carboxymethyl-topiramate (9-CMT) was used as the free acid to prepare immunogens and tracers in the following examples.

EXAMPLE 4

Preparation of N-Carboxymethyl-Topiramate: Bovine Serum Albumin Immunogen

This example describes preparation of an exemplary immunogen of this invention in which N-carboxymethyl topiramate, prepared as described in Example 1, was conjugated to bovine serum albumin (BSA) to form N-carboxymethyl-topiramate:bovine serum albumin (TGA:BSA).

A solution of 103 mg of N-carboxymethyl-topiramate and 34.9 mg N-hydroxysuccinimide (NHS) in 1 ml dimethylacetamide was chilled on an ice-methanol bath and treated with 100 µl of 3.15 M dicyclohexylcarbodiimide (in dimethylacetamide) to form a reaction mixture. The reaction mixture was stirred on the ice-methanol bath for 15 minutes and another 50 µl of dicyclohexylcarbodiimide solution was added. Stirring was continued while the reaction mixture was slowly brought to room temperature. Then the stirring was continued at room temperature overnight.

Following overnight stirring, the resulting active ester in the reaction mixture was coupled to bovine serum albumin. Bovine serum albumin was desalted prior to use in conjugation by G-25 SEPHADEX column chromatography in deionized water. A solution of 109 mg of previously desalted bovine serum albumin in a total of 15 ml water was chilled on an ice-water bath. The reaction mixture containing the active ester was added dropwise to the bovine serum albumin solution with stirring while maintaining the pH between 8 and 9 by adding 5% $K_2CO_3$ until the pH stabilized (approximately 1 hour).

The resulting reaction mixture was then kept overnight at 4° C. and solids were removed by centrifugation. The resulting supernatant fluid containing the conjugate was filtered through a 0.8 µm polycarbonate membrane and chromatographed over a 2.5×41 cm G-25 SEPHADEX column, equilibrated and eluted with 0.01 M potassium phosphate containing 0.15 M NaCl, pH 7.4. A total of 97 mg of conjugate (as protein) was obtained in final yield. The conjugate was stored frozen.

In this and the following examples, the protein concentration of immunogens was determined using a commercial biuret assay or by assuming that a 1 mg/ml solution of bovine serum albumin gave an absorbance of 0.67 at 280 nm in a 1 cm light path cell in phosphate-buffered saline (PBS) at pH 7.4.

EXAMPLE 5

Preparation of 9-Carboxymethyl-Topiramate: Bovine Serum Albumin Immunogen

This example describes preparation of another exemplary immunogen of this invention in which 9-carboxymethyl topiramate, prepared as described in Example 3, was conjugated to bovine serum albumin (BSA) to form 9-carboxymethyl-topiramate:bovine serum albumin (9-CMT:BSA).

206 mg of 9-carboxymethyl-topiramate and 70 mg N-hydroxysuccinimide were dissolved in 2 ml dimethylacetamide to form a reaction mixture. The reaction mixture was chilled on an ice-methanol bath and then 200 μl of 3.15 M dicyclohexylcarbodiimide in dimethylacetamide was added. The reaction mixture was stirred for 15 minutes on an ice-methanol bath and then an additional 100 μl of 3.15 M dicyclohexylcarbodiimide solution was added. The reaction mixture was stirred for an additional 10 minutes on an ice-methanol bath, and 0.025 ml of pyridine was added. The vessel containing the reaction mixture was removed from the bath and stirred for a few minutes at ambient temperature, and then stored overnight at –10° C. The next day, the reaction mixture was added dropwise with stirring to a solution of 200 mg of bovine serum albumin (previously desalted using a G-25 SEPHADEX column) in an ice bath. The pH of the reaction mixture was maintained between 8 and 9 by the addition of 5% $K_2CO_3$ until the pH stabilized. The reaction mixture was then stirred overnight at room temperature. The following day, solids were removed by centrifugation and the supernatant was filtered through a 0.2 μm filter to produce a clarified solution, which was desalted on a G-25 SEPHADEX column equilibrated in 10 mM potassium phosphate buffer (KPi), pH 7.4 containing 0.15 M NaCl. The yield of protein was 189 mg. The 9-CMT:BSA conjugate was stored frozen.

EXAMPLE 6

Preparation of N-(5-Carboxypentyl)-Topiramate: Bovine Serum Albumin Immunogen

This example describes preparation of another exemplary immunogen of this invention in which N-(5-carboxypentyl)-topiramate, prepared as described in Example 2, was conjugated to bovine serum albumin (BSA) to form N-(5-carboxypentyl)-topiramate:bovine serum albumin (TCA:BSA).

250 mg of the sodium salt of N-(5-carboxypentyl)-topiramate was dissolved in 2 ml of dimethylacetamide. 100 mg of N-hydroxysulfosuccinmide, sodium salt, was added to form a reaction and the reaction mixture was stirred for 10 minutes at room temperature. 200 μl of 3.15 M dicyclohexylcarbodiimide in dimethylacetamide was added, and the reaction mixture was stirred for 30 minutes at room temperature. 50 mg of N-hydroxysuccinimide was added to the reaction mixture, followed by 100 μl of 3.15 M dicyclohexylcarbodiimide solution. The reaction mixture was stirred for an additional 10 minutes, and 0.025 ml of pyridine was added. The reaction mixture was then stirred overnight at room temperature to produce an active ester.

The next day, the reaction mixture containing the active ester was added dropwise, with stirring, to a solution of 200 mg of bovine serum albumin (desalted prior to use by G-25 SEPHADEX column chromatography in water) in a total of 20 ml of water in an ice bath. The pH of the reaction mixture was maintained between 8 and 9 by the addition of 5% $K_2CO_3$ until the pH stabilized (about 2 hours). The resulting suspension was stored overnight at 4° C. Insoluble material was removed by filtration through a 0.2 μm polycarbonate membrane to produce a clarified solution. The clarified solution was chromatographed on a G-25 SEPHADEX column equilibrated in 10 mM KPi, pH 7.4 containing 0.15 M NaCl. The final yield of TCA:BSA conjugate was 189 mg.

EXAMPLE 7

Preparation of N-Carboxymethyl-Topiramate: (2-Aminoethyl)-Thioureido-Fluorescein This example describes preparation of N-carboxymethyl-topiramate:(2-aminoethyl)-thioureido-fluorescein which is useful as a tracer (TGA:FTED tracer) in a fluorescence polarization immunoassay.

22 mg of N-(carboxymethyl)-topiramate prepared as described in Example 1 was dissolved in 200 μl of dimethylacetamide. 20 mg of N-hydroxysuccinimide and 100 μl (100 μmol) of 1 M dicyclohexylcarbodiimide (in tetrahydrofuran) were added to form a reaction mixture, which was stirred for 90 minutes at room temperature to form the active ester (TGA:NOS).

2 ml MeOH and 0.1 ml of 1 N NaOH were added to a test tube. 21.6 mg of (2-aminoethyl)-thioureido-fluorescein (FTED) (prepared as described in Pourfarzeneh et al., *Clinical Chemistry* 26:730 (1980)) was dissolved in the methanol solution, and was subsequently added to the reaction mixture containing the active TGA:NOS ester. A precipitate formed which redissolved upon addition of 4×50 μl aliquots of 1 N NaOH. The pH of the resulting reaction mixture was 8.5. The reaction mixture was then stirred for 30 minutes at room temperature. The pH was maintained between 7.5 and 8.5 by the further addition, as necessary, of 1 N NaOH until the pH stabilized (approximately 1 hour). Samples of the reaction mixture were removed for chromatography after 1 hour and until as long as 4 hours.

The resulting N-carboxymethyl-topiramate:(2-aminoethyl)-thioureido-fluorescein was purified by thin layer chromatography on silica gel (SGF-250) in a solvent system of $CHCl_3$/MeOH/water (4+4+1) followed by chromatography on reverse phase thin layer plates (RPF-250) in a solvent system of MeOH/water/15 M $NH_4OH$ (25+75+2), as described below.

Throughout the examples, thin layer chromatography (TLC) was performed using silica gel plates containing a fluorescent indicator that absorbs at 254 nm. Plates were either 250 μm (referred to as SGF-250) or 1000 μm (referred to as SGF-1000) in thickness. C-18 reverse phase silica gel plates containing a fluorescent indicator that absorbs at 254 nm were 250 μm in thickness (referred to as RPF-250). Thin layer chromatography solvent systems and silica and reverse phase column chromatography solvent systems are all expressed in volume/volume composition. Some compounds were visualized on TLC plates by their absorbance (254 nm or 366 nm) or by using various spray indicators. Many of the fluorescent derivatives and colored compounds were visible without any treatment.

Approximate concentrations of purified tracers (N-acylamidofluoresceins) were determined assuming a molar extinction coefficient of 67,000 at the wavelength exhibiting maximum absorbance (490–500 nm, established by scanning) for a solution diluted in 0.05 M carbonate buffer, pH 9.6 and read in a 1 cm light path. Throughout the examples, the pH measurements in organic solvents were determined using water-moistened pH paper.

EXAMPLE 8

Preparation of N-Carboxymethyl-Topiramate: Fluorescein-Thiosemicarbazide

This example describes preparation of N-carboxymethyl-topiramate:fluorescein-thiosemi-carbazide which is useful as a tracer (TGA:FTSC tracer) in a fluorescence polarization immunoassay.

22.8 mg N-carboxymethyl-topiramate prepared as described in Example 1, was dissolved in 0.25 ml dimethylacetamide. 14.8 mg of N-hydroxysuccinimide was added, followed by 0.1 ml of 1 M dicyclohexylcarbodiimide (in tetrahydrofuran) to form a reaction mixture. The reaction mixture was stirred overnight at room temperature to from the active ester.

Fluorescein thiosemicarbazide (10 mg, obtained from Sigma Chemical Company) was dissolved in (0.1 ml MeOH+0.05 ml 1 N NaOH) and added to the reaction mixture containing the active ester of N-carboxymethyl-topiramate. The reaction mixture was stirred for 15 minutes, at which time 0.05 ml of 10% triethylamine (in MeOH) was added and stirring was continued for another 2 hours at room temperature to form N-carboxymethyl-topiramate:fluorescein-thiosemicarbazide. The N-carboxymethyl-topiramate: fluorescein-thiosemicarbazide was purified by successive thin layer chromatography steps on silica gel plates (SGF-250) in the solvent MeOH/CHCl$_3$/H$_2$O (4+4+1) and then on reverse phase plates (RPF-250) in the solvent system MeOH/water/triethylamine (20+80+1).

EXAMPLE 9

Preparation of (2-Aminoethyl)-Ureido-Fluorescein

This example describes preparation of (2-aminoethyl)-ureido-fluorescein (FAMCO-E) which was conjugated to topiramate analogs as described in the following examples.

To prepare FAMCO-E, 3.25 g of fluoresceinamine isomer I was dissolved in 17.5 ml of dimethylacetamide and 2.5 g of 1,1'-carbonyldiimidazole was added to form a reaction mixture. (Isomers I and II of fluorescein derivatives are defined as having substituents at positions 5 or 6 of the fluorescein nucleus, respectively. Unless otherwise stated, all fluorescein derivatives described are isomer I derivatives. However, Isomer II or mixtures of I and II can be used to prepare suitable reagents.) The reaction mixture was stirred for 3 hours at room temperature. 5 ml of ethylenediamine was added to 500 ml of methylene chloride in a 1 liter flask to form an ethylenediamine solution, and this solution was chilled on an ice-methanol bath. The 1,1'carbonyldiimidazole/fluoresceinamine reaction mixture was then added dropwise with vigorous stirring to the chilled ethylenediamine solution. An orange precipitate formed. The reaction mixture was stirred overnight at room temperature. The orange precipitate was collected on a Buchner funnel and washed extensively in succession with methylene chloride, methylene chloride/acetone/MeOH (100+10+1 v/v), and methylene chloride. The washed precipitate product was dried, then suspended in acetone, filtered, washed with petroleum ether, and the crude powder was allowed to air dry. 5 ml MeOH and 0.15 ml of 15 M NH$_4$OH was added to 0.5042 g of the dry, crude powder to produce a clear, deep red solution. This solution was added dropwise with stirring, to 200 volumes of MeOH/water/acetic acid (10+90+1 v/v). Some precipitation occurred. Insoluble material was collected, dissolved in MeOH/15 M NH$_4$OH (100+2, v/v) and again added dropwise with stirring to 200 volumes of MeOH/water/acetic acid (10+90+1 v/v). The precipitate was collected and discarded. The pooled MeOH/water/acetic acid solutions were filtered for clarification and subjected to low pressure C18 reverse phase chromatography in a column equilibrated with MeOH/water/acetic acid (10+90+1). FAMCO-E bound to the column and was eluted with MeOH/water/acetic acid (15+85+1). The eluted FAMCO-E was concentrated by recycling on the C18 column under the same conditions except that a 7.5% methanol wash step (to remove the acetic acid) was performed prior to elution, and elution was achieved with methanol (100%). The eluted fractions containing the FAMCO-E were pooled and sufficient triethylamine was added to give a pH between 8 and 9. The purified FAMCO-E was stored as a solution in methanol at −10° C.

EXAMPLE 10

Preparation of N-Carboxymethyl-Topiramate: (2-Aminoethyl)-Ureido-Fluorescein

This example describes preparation of N-carboxymethyl-topiramate:(2-aminoethyl)-ureido-fluorescein which is useful as a tracer (TGA:FAMCO-E tracer) in a fluorescence polarization immunoassay.

10 mg of N-carboxymethyl-topiramate prepared as described in Example 1 and 5 mg of N-hydroxysuccinimide were dissolved in 0.2 ml of dimethylacetamide. 0.05 ml of 1 M dicyclohexylcarbodiimide (in tetrahydrofuran) was added and the resulting reaction mixture was stirred for 2.5 hours to produce an active ester. 0.1 ml of the reaction mixture containing the active ester was added to 0.5 ml of a solution of (2-aminoethyl)-ureido-fluorescein (FAMCO-E), prepared as described in Example 9. After 15 minutes, 5 μl of triethylamine was added to maintain the pH between 8 and 9. The reaction mixture was incubated for 60 minutes at room temperature. The resulting N-carboxymethyl-topiramate:(2-aminoethyl)-ureido-fluorescein was then purified in successive thin layer chromatography steps on silica gel (SGF-250) in solvent system CHCl$_3$ /MeOH/water (4+4+1) and reversed phase thin layer chromatography in solvent system MeOH/water/15 M NH$_4$OH (20+80+2).

EXAMPLE 11

Preparation of N-Carboxymethyl-Topiramate: Glycyl-Fluoresceinamine

This example describes preparation of N-carboxymethyl-topiramate:glycyl-fluoresceinamine which is useful as a tracer (TGA:Gly-FAM tracer) in a fluorescence polarization immunoassay.

5 mg of aminoacetamido-fluorescein (Molecular Probes, Inc., Eugene, Oreg.) was dissolved in 0.1 ml of dimethylacetamide. 0.15 ml of an active ester of N-carboxymethyl-topiramate, prepared as described in Example 10, was added, and the resulting reaction was allowed to proceed for 1 hour at room temperature. The pH was maintained between 6.5 and 8 by adding small volumes of triethylamine. The resulting N-carboxymethyl-topiramate:glycyl-fluoresceinamine was purified in successive steps of thin layer chromatography on silica gel (SGF-250) in solvent system $CHCl_3$/MeOH/water (4+4+1) and reverse phase (RPF-250) in solvent system MeOH/water/15 M $NH_4OH$ (20+80+2).

EXAMPLE 12

Preparation of N-(5-Carboxypentyl)-Topiramate: (2-Aminoethyl)-Thioureido-Fluorescein This example describes preparation of N-(5-carboxypentyl)-topiramate:(2-aminoethyl)-thioureido-fluorescein which is useful as a tracer (TCA:FTED tracer) in a fluorescence polarization immunoassay.

250 mg of the sodium salt of N-(5-carboxypentyl)-topiramate, prepared as described in Example 2, was added to 2 ml dimethylacetamide. 0.1 g of N-hydroxysulfosuccinimide, sodium salt, was added, the resulting reaction mixture was stirred for 10 minutes, and 0.2 ml of 3.15 M dicyclohexylcarbodiimide (in dimethylacetamide) was added. The reaction mixture was stirred for 30 minutes and 0.05 g of N-hydroxysuccinimide and 0.1 ml of 3.15 M dicyclohexylcarbodiimide (in dimethylacetamide) were added in succession. After stirring 10 more minutes, 0.025 ml of pyridine was added, and the reaction mixture was stirred overnight at room temperature to form the active ester.

An excess of (2-aminoethyl)-thioureido-fluorescein (in methanol made alkaline with NaOH) was added to 0.5 ml of the reaction mixture containing the active ester. The reaction was allowed to proceed for 30 minutes at room temperature. The resulting N-(5-carboxypentyl)-topiramate:(2-aminoethyl)-thioureido-fluorescein was purified in successive steps of thin layer chromatography on silica gel (SGF-250) in solvent system $CHCl_3$/MeOH/water (4+4+1) and reverse phase (RPF-250 plates) in solvent system MeOH/water/15 M $NH_4OH$ (27.5+72.5+2).

EXAMPLE 13

Preparation of N-(5-Carboxypentyl)-Topiramate: (2-Aminoethyl)-Ureido-Fluorescein This example describes preparation of N-(5-carboxypentyl)-topiramate:(2-aminoethyl)-ureido-fluorescein which is useful as a tracer (TCA:FAMCO-E tracer) in a fluorescence polarization immunoassay.

473 mg of N-(5-carboxypentyl)-topiramate, sodium salt, prepared as described in Example 2, was added to 5 ml of dimethylacetamide to form a reaction mixture. 399 mg of N-hydroxysuccinimide was added and the reaction mixture was stirred for 5 minutes at room temperature and then chilled by stirring for 5 minutes in an ice bath. 1 ml of 1 M dicyclohexyldicarbodiimide (in tetrahydrofuran) was added, and the reaction mixture was stirred for 15 minutes on an ice bath and then overnight at room temperature.

20 ml of MeOH containing 0.108 mmol of FAMCO-E, prepared as described in Example 9, was added to the reaction mixture. The pH was maintained between 8 and 9 by adding small volumes of triethylamine. The reaction was allowed to proceed for 2 hours at room temperature to produce TCA:FAMCO-E tracer, then the reaction mixture was diluted with 9 volumes of 0.5% $NH_4OH$ (0.075 M) and applied to a low pressure C18 HPLC sorbent column (20 g) equilibrated in MeOH/water/15 M $NH_4OH$ (10+90+0.5). The column was washed with approximately 10 column volumes of MeOH/water/15 M $NH_4OH$ (10+90+0.5) to remove contaminants, and then the TCA:FAMCO-E tracer was eluted with MeOH/water/15 M $NH_4OH$ (15+85+0.5). The TCA:FAMCO-E tracer was concentrated by chromatography on C18 under similar conditions but elution was performed with methanol/triethylamine (10+0.04 v/v). The TCA:FAMCO-E tracer was then purified by thin layer chromatography on silica gel (SGF-1000) plates in the solvent system MeOH/$CHCl_3$/water (4+4+1), where the tracer exhibited an $R_f$ of about 0.6. The tracer band was eluted from the silica plates with methanol/triethylamine (10+0.04), the pH of the solution was adjusted to between 8 and 9 with triethylamine, and the tracer was stored at $-10°$ C.

EXAMPLE 14

Preparation of N-(5-Carboxypentyl)-Topiramate: (2-Aminoethyl)-Ureido-Fluorescein, Isomer II This example describes preparation of N-(5-carboxypentyl)-topiramate:(2-aminoethyl)-ureido-fluorescein, isomer II which is useful as a tracer (TCA:FAMCO-E tracer, isomer II) in a fluorescence polarization immunoassay.

The FAMCO-E, isomer II used in this example was synthesized and purified using the methods described for preparing FAMCO-E, isomer I in Example 9, except that fluoresceinamine isomer II (6-aminofluorescein) was used in the synthesis instead of fluoresceinamine isomer I (5-aminofluorescein) and the crude powder was purified using thin layer chromatography on reverse phase plates using the solvent system methanol/water/15 M $NH_4OH$ (10+90+2). The FAMCO-E was stored at $-10°$ C. as a solution in methanol.

25 mg of N-(5-carboxypentyl)-topiramate, sodium salt, prepared as described in Example 2, was added to 0.25 ml dimethylacetamide to form a reaction mixture. 10 mg of N-hydroxysuccinimide was added. The reaction mixture was stirred and chilled on an ice bath, and then 0.05 ml of 1 M dicyclohexylcarbodiimide (in tetrahydrofuran) was added. The reaction mixture was stirred for 30 minutes more on an ice bath and then for 2 hours at room temperature. An excess of FAMCO-E (isomer II) solution was added and the reaction was allowed to proceed for 1 hour at room temperature, with the pH maintained above 7 by the addition of triethylamine as necessary. The reaction mixture was incubated for 1 hour at ambient temperature to produce TCA:FAMCO-E tracer, isomer II. The tracer was then purified by thin layer chromatography on reverse phase plates (RPF-250) in the solvent system MeOH/water/15 M $NH_4OH$ (25+75+2).

EXAMPLE 15

Preparation of 9-Carboxymethyl-Topiramate: (2-Aminoethyl)-Ureido-Fluorescein

This example describes preparation of 9-carboxymethyl-topiramate:(2-aminoethyl)-ureido-fluorescein which is useful as a tracer (9-CMT:FAMCO-E tracer) in a fluorescence polarization immunoassay.

12.4 mg of 9-carboxymethyl-topiramate, prepared as described in Example 3, was added to 0.20 ml of dimethylacetamide. 12.9 mg of N-hydroxysuccinimide was added, followed by 0.05 ml of 1 M dicyclohexylcarbodiimide (in tetrahydrofuran) and the reaction mixture was incubated at room temperature for 2.5 hours. An excess of FAMCO-E (in methanol) was added, followed by addition of triethylamine (9 µl) to adjust the pH to 8.5. The reaction mixture was stirred for 60 minutes at room temperature and then 0.05 ml of 1 N NaOH was added, and the reaction mixture was mixed by shaking. After an additional 15 minutes incubation at room temperature, 0.05 ml of 1 N HCl was added to give a final pH of 8.5 to produce 9-CMT:FAMCO-E tracer. The tracer was purified by silica gel thin layer chromatography (SGF-250) in the solvent system $CHCl_3$/MeOH/water (50+50+2.5).

EXAMPLE 16

Preparation of N-Carboxymethyl-Topiramate: 5-(((N-(Biotinoyl)Amino)Hexanoyl)Amino) Pentylamine This example describes preparation of N-carboxymethyl-topiramate:5-(((N-(biotinoyl)-amino)-hexanoyl)amino) pentylamine conjugate (TGA-R:biotin) which is useful as a tracer in a biotin-avidin-based immunoassay.

9 mg of N-carboxymethyl-topiramate (prepared as described in Example 1), 3.3 mg of N-hydroxysuccinimide, and 8.4 mg of 5-(((N-(biotinoyl)amino)-hexanoyl)amino) pentylamine (Molecular Probes, Eugene, Oreg.) were combined in 0.3 ml of dimethylacetamide to form a reaction mixture. The reaction mixture was chilled on an ice/methanol bath and 0.025 ml of 1 M dicyclohexylcarbodiimide (in tetrahydrofuran) was added. The reaction mixture was stirred a few minutes in the ice/methanol bath, and then 0.05 ml of methanol was added. The reaction mixture was incubated overnight at room temperature. Upon chilling, crystals formed. The reaction mixture was placed at −20° C. for 1 hour, and insoluble material was removed by centrifugation. The N-carboxymethyl-topiramate:biotin derivative was purified from the soluble fraction by thin layer chromatography on silica gel (SGF-250) using the solvent system MeOH/$CHCl_3$/water (20+80+1). The product was visualized by spraying a small portion of the TLC plate with a solution of 0.2% $KMnO_4$ in 1 N $H_2SO_4$. The appropriate band was scraped from the remainder of the plate (not sprayed for visualization) and was eluted from the silica with methanol. A competitive avidin-biotin fluorescence polarization assay was used to estimate the concentration of biotin (as topiramate conjugate) in the preparation. The concentration was estimated to be approximately 1.2 mM. The TGA:R-biotin conjugate was stored as a stock solution in methanol at −10° C.

EXAMPLE 17

ELISA Immunoassay Using N-Carboxymethyl-Topiramate:5-(((N-(Biotinoyl) Amino) Hexanoyl) Amino)Pentylamine Conjugate This example describes an exemplary ELISA immunoassay for topiramate using N-carboxymethyl-topiramate:5-(((N-(biotinoyl)amino)hexanoyl)amino)pentylamine conjugate (TGA:R-biotin).

A hybridoma cell line designated 7B10 producing monoclonal anti-topiramate antibody was produced from the spleen cells of a Balb/c female mouse immunized with N-carboxymethyl-topiramate:BSA (TGA:BSA), prepared as described in Example 4. The animal was immunized once intraperitoneally with 50 µg of TGA:BSA emulsified in complete Freund's adjuvant. Thereafter, the animal was injected intraperitoneally every 3 to 5 weeks with 50 µg of TGA:BSA emulsified in incomplete Freund's adjuvant for a total of 5 immunizations. The animal was then boosted once with 50 µg of N-(5-carboxypentyl)-topiramate:BSA (prepared as described in Example 6) intraperitoneally. Spleen cells were used to prepare hybridoma cell lines using the NS1 mouse myeloma line as a fusion partner. Hybridoma culture media were screened for the presence of topiramate antibodies using the ELISA procedure described below. Antibodies which bound to TGA:R-biotin immobilized on streptavidin but not to streptavidin alone were chosen for further characterization. The 7B10 cell line was chosen for cloning based upon the screening results, and subclone 7B10.2 and a clone of the latter, 7B10.2.1, were established and cryopreserved.

A solution of 0.1 µg/ml of streptavidin (Molecular Probes, Eugene, Oreg.) was prepared in PBS (0.01 M potassium phosphate buffer, pH 7.4 containing 0.15 M NaCl and 0.01% thimersol) and 0.1 ml of the streptavidin solution was pipetted into each of the wells of a Pierce IMMUNOWARE polystyrene multiwell plate. The streptavidin solution was incubated on the plate overnight at 4° C. All other steps were performed at ambient temperature.

The wells were washed 4 times with PBS containing 0.1% (v/v) TWEEN 20 (hereafter, PBS/tween), and flicked to remove all bulk fluid. A stock solution of TGA:R-biotin, prepared as described in Example 16 (approximately 1.2 mM in methanol), was diluted 1/5000 in PBS/tween and 0.1 ml of the diluted TGA:R-biotin solution was added to all the wells. After 3 hours at room temperature, the TGA:R-biotin solution was aspirated, and the plate washed 4 times with PBS/tween. Stock solutions of topiramate in PBS/tween were prepared to give topiramate standards having concentrations of 20, 200, and 2000 ng/ml. Topiramate standards (0.05 ml) were added to the wells to give final concentrations of 0, 10, 100, and 1000 ng/ml. The topiramate metabolite, 9-hydroxy-topiramate (Ortho/McNeil Pharmaceuticals, catalog no. RJW-38214-000), was added in a series of wells to give final concentrations of 100, 1000, and 10,000 ng/ml.

Cell culture medium from hybridoma cell line 7B10 was diluted 1/128 in PBS/tween, and 0.05 ml was added to each well (final antibody dilution 1/256). The plate was incubated for 2 hours at ambient temperature. The plate was then washed 4 times with PBS/tween. Goat anti-mouse IgG-horseradish peroxidase conjugate (CALTAG Laboratories, South San Francisco, Calif.) was diluted 1/500 in PBS/tween and added to each well (0.1 ml). After 2 hours at room temperature, the plate was washed 4 times with PBS/tween, and the peroxidase activity was assayed by adding 0.1 ml of 0.31 mg/ml tetramethylbenzidine containing 2.6 mM $H_2O_2$ in 0.125 M sodium acetate/0.075 M citric acid buffer, pH 4.0. After 4 minutes, the reaction was stopped by adding 0.1 ml of 1 M sulfuric acid to each well. The yellow product was read in a Dynatech MR5000 plate reader at 450 nm. The results of the assay are illustrated below in Table 3. In the table, $B/B_O$ is the ratio of the absorbance value at 450 nm for the test sample (B) divided by the absorbance value obtained in the absence of competing analyte ($B_O$).

TABLE 3

| | $A_{450\ nm}$ | $B/B_o$ |
|---|---|---|
| Analyte (ng/ml) | | |
| Topiramate | | |
| 0 | 0.696 | 1.00 |
| 10 | 0.599 | 0.86 |
| 100 | 0.247 | 0.35 |
| 1,000 | 0.028 | 0.04 |
| 10,000 | ND* | ND |
| 9-Hydroxy- | | |
| Topiramate | | |
| 0 | 0.659 | 1.00 |
| 10 | ND | ND |
| 100 | 0.663 | 1.01 |
| 1,000 | 0.651 | 0.99 |
| 10,000 | 0.466 | 0.71 |

*ND: not determined

As shown in Table 3, topiramate inhibited antibody binding greater than 50% at less than 100 ng/ml, while less than 50% inhibition was observed with 10,000 ng/ml of the metabolite 9-hydroxy-topiramate. The assay demonstrated that the crossreactivity of the 7B10 monoclonal antibody for the topiramate metabolite product 9-hydroxy-topiramate was less than 1%.

EXAMPLE 18

Fluorescence Polarization Immunoassay Using N-Carboxymethyl-Topiramate: (2-Aminoethyl)-Thioureido-Fluorescein This example describes an exemplary fluorescence polarization immunoassay (FPIA) for topiramate using N-carboxymethyl-topiramate:(2-aminoethyl)-thioureido-fluorescein as a tracer (TGA:FTED tracer). An exemplary automated fluorescence polarization immunoassay system used in this and the following examples is described below, followed by a description of preparation of antibodies used in the examples.

Automated Fluorescence Polarization Immunoassay

The fluorescence polarization immunoassay was performed using an automated TDx® polarization analyzer (Abbott Laboratories of Irving, Tex.) using a competitive immunoassay format. Reagents to perform the automated assay included anti-analyte antibody (anti-topiramate antibody) or "A", a fluorescein: topiramate analog conjugate (tracer or "T"), and a pretreatment buffer or "B". The calibration of the automated assay described in the examples was achieved with a series of six calibrators that include specified concentrations of topiramate spiked into human serum.

The automated assay is described in detail in literature available from Abbott Laboratories, Irving, Tex. All examples described herein used the "mode 1" pipetting sequence on the instrument. Patient samples (neat serum or plasma) are placed in plastic sample cups in a circular carousel designed for the TDx® instrument. The carousel is placed in the instrument along with the reagent kit containing the A, T, and B. In the first cycle of the assay, a predilution of the patient sample with TDx Systems® buffer is made in a second well in the sample cup, and half of the total volume of the sample (patient sample diluted in buffer) is placed in the sample cuvette (a total of about 1 ml) along with 0.025 ml of the pretreatment buffer B from the reagent kit. A blank fluorescence reading is taken. In the second pipetting cycle, a second volume of the diluted patient sample is added, along with 0.025 ml of tracer (typically 0.5–10 pmol per tube) and 0.025 ml of antibody in a total volume of approximately 2 ml in the cuvette. After the reaction has gone to completion, the analyzer reads the polarization of fluorescence in the glass cuvette and compares that value with a calibration curve established by measuring six concentrations of drug formulated in human serum (calibrators). The equivalent of 0.5 to 5 microliters of patient serum or plasma is a typical sample size (added to the 2 ml total sample volume) in the automated assay. The polarization of fluorescence is reported in millipolarization units (mP). The TDx® analyzer automatically calculates the concentration of analyte in the sample by comparison with the calibration curve.

In the examples, the anti-topiramate antibody dilutions for both the antibody reagent in the immunoassay kit (an 80× stock solution) and the final dilution in the glass cuvette are described. Tracer diluents and pretreatment buffers (B) are described in the examples as the 80× stock solutions of the reagents present in the immunoassay kit.

Polyclonal Sheep Anti-topiramate Antibodies

All immunogens were prepared as emulsions in complete Freund's adjuvant for the first injection, and in incomplete Freund's adjuvant for subsequent injections. Animals were immunized either subcutaneously with 1 mg of immunogen (as protein) or directly in the lymph node with 50 µg of immunogen. Animals were typically injected every 3 weeks. Sera were screened using ELISA as described for the mouse monoclonal preparation above, with the exception that sheep antibodies that bound to TGA:R-biotin immobilized on streptavidin in microtiter plates were detected using a rabbit anti-sheep IgG-horse radish peroxidase conjugate (Chemicon International, Temecula, Calif.).

Anti-sera from 3 sheep were used in the examples. The sheep were immunized as described below.

| Sheep No. | Immunogen | Immunization Route |
|---|---|---|
| 787 | TGA:BSA | Lymph Node |
| 662 | 9CMT:BSA | Subcutaneous |
| 650 | TCA:BSA | Subcutaneous |

Three preparations of antibody derived from sheep no. 787 were used in the examples. These preparations are coded as 787-1, 787-2, and 787-3. TGA:BSA used to immunize sheep 787 was prepared as described in Example 4. 9-CMT:BSA used to immunize sheep 662 was prepared as described in Example 5. TCA:BSA used to immunize sheep 650 was prepared as described in Example 6.

In a fluorescence polarization immunoassay using TGA:FTED tracer, a calibration curve was prepared using sheep antibody no. 787-1, prepared as described above and diluted 1/24 (final dilution 1/1920) in TDx Systems® buffer (0.1 M KPi, pH 7.5, containing 0.1% sodium azide and 0.01 mg/ml bovine gamma globulin, pH 7.0–7.5). TGA:FTED tracer, prepared as described in Example 7, and diluted in 0.01 M KPi, 0.15 M NaCl, 0.1% w/v sodium azide, 1 mg/ml bovine gamma globulin, pH 7.4–7.5 was used as the tracer. The pretreatment buffer was TDx Systems® buffer. The sample volume for the calibrators was 1 µl.

Table 4 shows polarization values that were obtained using six topiramate calibrators. In this and the following tables, polarization values are given in millipolarization units.

TABLE 4

| Topiramate (μg/ml) | Polarization |
| --- | --- |
| 0 | 235.09 |
| 2.5 | 222.06 |
| 5.0 | 208.12 |
| 10.0 | 184.83 |
| 25.0 | 141.89 |
| 50.0 | 110.42 |

EXAMPLE 19

Fluorescence Polarization Immunoassay Using N-Carboxymethyl-Topiramate: Fluorescein-Thiosemicarbazide This example describes an exemplary fluorescence polarization immunoassay for topiramate using N-carboxymethyl-topiramate:fluorescein-thiosemicarbazide prepared as described in Example 8 as a tracer (TGA:FTSC tracer). The fluorescence polarization immunoassay was performed using an automated TDx® polarization analyzer to prepare a calibration curve using TGA:FTSC tracer as described in Example 18 with the following exceptions. In this example, the antibody was sheep antibody no. 787-1, prepared as described in Example 18 and diluted 1/24 (final antibody dilution 1/1920). The tracer diluent was TDx Systems® buffer. Sample volume for the calibrators was 1.3 μl. The results of the assay are illustrated below in Table 5.

TABLE 5

| Topiramate (μg/ml) | Polarization |
| --- | --- |
| 0 | 224.54 |
| 2.5 | 212.83 |
| 5.0 | 198.29 |
| 10.0 | 178.85 |
| 25.0 | 145.09 |
| 50.0 | 122.07 |

EXAMPLE 20

Fluorescence Polarization Immnunoassay Using N-Carboxymethyl-Topiramate: (2-Aminoethyl)-Ureido-Fluorescein This example describes an exemplary fluorescence polarization immunoassay for topiramate using N-carboxymethyl-topiramate:(2-aminoethyl)-ureido-fluorescein prepared as described in Example 10 as a tracer (TGA:FAMCO-E tracer). The fluorescence polarization immunoassay was performed using an automated TDx® polarization analyzer to prepare a calibration curve using TGA:FAMCO-E tracer as described in Example 18 with the following exceptions. In this example, the antibody was antibody no. 787-2, prepared as described in Example 18 and diluted 1/80 (final antibody dilution 1/6400). The results of the assay are illustrated below in Table 6.

TABLE 6

| Topiramate (μg/ml) | Polarization |
| --- | --- |
| 0 | 223.68 |
| 2.5 | 194.69 |
| 5.0 | 173.33 |
| 10.0 | 145.51 |
| 25.0 | 109.34 |
| 50.0 | 86.36 |

EXAMPLE 21

Fluorescence Polarization Immunoassay Using N-Carboxymethyl-Topiramate: Glycyl-Fluoresceinamine This example describes an exemplary fluorescence polarization immunoassay for topiramate using N-carboxymethyl-topiramate:glycyl-fluoresceinamine prepared as described in Example 11 as a tracer (TGA:Gly-FAM tracer). The fluorescence polarization immunoassay was performed using an automated TDx® polarization analyzer to prepare a calibration curve using TGA:Gly-FAM tracer as described in Example 18 with the following exceptions. In this example, the antibody was antibody no. 787-2, prepared as described in Example 18 and diluted 1/80 (final dilution 1/6400). The results of the assay are illustrated below in Table 7.

TABLE 7

| Topiramate (μg/ml) | Polarization |
| --- | --- |
| 0 | 193.28 |
| 2.5 | 180.25 |
| 5.0 | 162.38 |
| 10.0 | 141.51 |
| 25.0 | 109.17 |
| 50.0 | 89.10 |

EXAMPLE 22

Fluorescence Polarization Immunoassay Using N-(5-Carboxypentyl)-Topiramate: (2-Aminoethyl)-Thioureido-Fluorescein This example describes an exemplary fluorescence polarization immunoassay for topiramate using N-(5-carboxypentyl)-topiramate:(2-aminoethyl)-thioureido-fluorescein, prepared as described in Example 12 as a tracer (TCA:FTED tracer). The fluorescence polarization immunoassay was performed using an automated TDx® polarization analyzer to prepare a calibration curve using TCA:FTED tracer as described in Example 18 with the following exceptions. In this example, antibody no. 787-2, prepared as described in Example 18 and diluted 1/100 (final dilution 1/8000). The tracer was diluted in 0.01 M KPi, pH 7.5, 0.10% w/v sodium azide, 1 mg/ml bovine gamma globulin. The results of the assay are illustrated below in Table 8.

TABLE 8

| Topiramate (μg/ml) | Polarization |
| --- | --- |
| 0 | 245.72 |
| 2.5 | 200.79 |
| 5.0 | 172.41 |
| 10.0 | 139.21 |

TABLE 8-continued

| Topiramate (µg/ml) | Polarization |
|---|---|
| 25.0 | 97.70 |
| 50.0 | 75.50 |

EXAMPLE 23

Fluorescence Polarization Immunoassay Using N-(5-Carboxypentyl)-Topiramate: (2-Aminoethyl)-Ureido-Fluorescein This example describes an exemplary fluorescence polarization immunoassay for topiramate using N-(5-carboxypentyl)-topiramate:(2-aminoethyl)-ureido-fluorescein prepared as described in Example 13 as a tracer (TCA:FAMCO-E tracer). The fluorescence polarization immunoassay was performed using an automated TDx® polarization analyzer to prepare a calibration curve using TCA:FAMCO-E tracer as described in Example 18 with the following exceptions. In this example, antibody no. 787-2, prepared as described in Example 18 and diluted 1/90 (final dilution 1/7200). The tracer diluent was TDx Systems® buffer. Sample volume for the calibrators was 0.7 µl. The results of the assay are illustrated below in Table 9.

TABLE 9

| Topiramate (µg/ml) | Polarization |
|---|---|
| 0 | 240.92 |
| 2.5 | 204.13 |
| 5.0 | 180.44 |
| 10.0 | 150.23 |
| 25.0 | 109.96 |
| 50.0 | 87.83 |

EXAMPLE 24

Fluorescence Polarization Immunoassay Using N-(5-Carboxypentyl)-Topiramate: (2-aminoethyl)-Ureido-Fluorescein, Isomer II This example describes an exemplary fluorescence polarization immunoassay for topiramate using N-(5-carboxypentyl)-topiramate:(2-aminoethyl)-ureido-fluorescein, isomer II prepared as described in Example 14 as a tracer (TCA:FAMCO-E tracer, isomer II). The fluorescence polarization immunoassay was performed using an automated TDx® polarization analyzer to prepare a calibration curve using TCA:FAMCO-E tracer, isomer II as described in Example 18 with the following exceptions. In this example, antibody no. 787-3, prepared as described in Example 18 and diluted 1/68 (final dilution 1/5440) in 0.1 M KPi, 0.1% sodium azide, pH 7.4–7.6. The tracer diluent was 0.1 M KPi, 0.005w dioctylsodiumsulfosuccinate (DOSS), 0.1% w/v sodium azide, 1 mg/ml bovine gamma globulin. The pretreatment buffer was 20 mM KPi, pH 4.0, 0.1% DOSS. Sample volume for the calibrators was 1.4 µl. The results of the assay are illustrated below in Table 10.

TABLE 10

| Topiramate (µg/ml) | Polarization |
|---|---|
| 0 | 227.24 |
| 2 | 184.65 |
| 4 | 157.73 |
| 8 | 128.78 |
| 16 | 100.50 |
| 32 | 76.86 |

EXAMPLE 25

Fluorescence Polarization Immunoassay Using 9-Carboxymethyl-Topiramate: (2-Aminoethyl)-Ureido-Fluorescein This example describes an exemplary fluorescence polarization immunoassay for topiramate using 9-carboxymethyl-topiramate:(2-aminoethyl)-ureido-fluorescein prepared as described in Example 15 as a tracer (9-CMT:FAMCO-E tracer). The fluorescence polarization immunoassay was performed using an automated TDx® polarization analyzer to prepare a calibration curve using 9-CMT:FAMCO-E tracer as described in Example 18 with the following exceptions. In this example, the antibody was sheep antibody no. 662, prepared as described in Example 18 and diluted 1/10 (final dilution 1/800). The tracer diluent was TDx Systems® buffer. Sample volume for the calibrators was 5 µl. The results of the assay are illustrated below in Table 11.

TABLE 11

| Topiramate (µg/ml) | Polarization |
|---|---|
| 0 | 202.90 |
| 4.0 | 185.60 |
| 8.0 | 174.58 |
| 16.0 | 159.91 |
| 32.0 | 143.77 |
| 64.0 | 124.42 |

EXAMPLE 26

Fluorescence Polarization Immunoassay Using N-Carboxymethyl-Topiramate: (2-Aminoethyl)-Ureido-Fluorescein This example describes an exemplary fluorescence polarization immunoassay for topiramate using N-carboxymethyl-topiramate:(2-aminoethyl)-ureido-fluorescein prepared as described in Example 10 as a tracer (TGA:FAMCO-E tracer). The fluorescence polarization immunoassay was performed using an automated TDx® polarization analyzer using TGA:FAMCO-E tracer to prepare a calibration curve as described in Example 18 with the following exceptions. In this example, the antibody was sheep antibody no. 650, prepared as described in Example 18 and diluted 1/10 (final dilution 1/800). The tracer diluent was TDx Systems® buffer. Sample volume for the calibrators was 2 µl. The results of the assay are illustrated below in Table 12.

TABLE 12

| Topiramate (μg/ml) | Polarization |
|---|---|
| 0 | 229.22 |
| 2 | 213.93 |
| 4 | 203.44 |
| 8 | 186.89 |
| 16 | 167.79 |
| 32 | 145.54 |

EXAMPLE 27

Comparison of Fluorescence Polarization Immunoassay and Gas Chromatographic Analysis of Topiramate This example describes a comparison of results of an exemplary florescence polarization immunoassay for topiramate with gas chromatography analysis using 117 plasma samples obtained from patients undergoing topiramate therapy.

The fluorescence polarization immunoassay used N-(5-caboxypentyl)-topiramate:(2-aminoethyl)-ureido-fluorescein tracer (TCA:FAMCO-E tracer) diluted in 0.1 M KPi, pH 7.4–7.6, 0.005% dioctylsodiumsulfosuccinate (DOSS), 0.1% w/v sodium azide, 1 mg/ml bovine gamma globulin. The antibody used was sheep antibody no. 787-3, prepared as described in Example 18 and diluted 1/68 (final dilution 1/5440) in 0.1 M KPi, pH 7.4–7.6, containing 0.1% w/v sodium azide. The pretreatment buffer was 20 mM KPi, pH 4.0, containing 0.1% dioctylsodiumsulfosuccinate (DOSS). The sample volume was 1.4 μl. calibration curve was established on the TDx® analyzer using the automated assay described in Example 18. The six calibrators were 0, 2, 4, 8, 16, and 32 μg/ml topiramate in human serum.

Samples were assayed in duplicate and the average values were used for the method of comparison.

The gas chromatographic method with nitrogen phosphorus detection was performed as described in Cooper, J M, Stubbs, R J and Palmer, M E, *Pharmaceutical Research* 8(10 Suppl.):S19 (1991). This method is technically demanding and was found to be sensitive, precise, and specific.

A direct comparison of the two methods was performed using calibration over a range of 2–32 μg/ml topiramate for the samples. A comparison of the results of the fluorescence polarization immunoassay (FPIA) with the gas chromatography on the 117 patient samples demonstrated the relationship:

(FPIA value)=–0.147+0.985 (GC value) r=0.9935

As demonstrated in this example, the fluorescence polarization immunoassay method using exemplary reagents of this invention provided an excellent correlation to the gas chromatographic method of analysis of topiramate.

EXAMPLE 28

Determination of Antibody Crossreactivity

This example describes a determination of the amount of crossreactivity of polyclonal and monoclonal antibody compositions with the topiramate metabolite 9-hydroxy-topiramate.

Two polyclonal antibody preparations made in sheep (sheep antibody nos. 662 and 787-3) were prepared as described in Example 18. Preparation of a standard curve using sheep antibody no. 662 and 9-carboxymethyl-topiramate:(2-aminoethyl)-ureido-fluorescein tracer (9-CMT:FAMCO-E tracer) is described in Example 25. Known amounts of 9-hydroxy-topiramate in human serum were assayed using that calibration curve.

Preparation of standard curves for sheep antibody no. 787-3 and N-(5-carboxypentyl)-topiramate: (2-aminoethyl)-ureido-fluorescein tracer (TCA:FAMCO-E tracer) was performed as described in Example 27. Known amounts of 9-hydroxy-topiramate in human serum were assayed using those calibration curves.

The observed concentration of topiramate was used to calculate the amount of crossreactivity of the antibody preparations with 9-hydroxy-topiramate as follows. The (% crossreactivity) equals (100 times the observed concentration of topiramate in μg/ml) divided by (the concentration of added 9-hydroxy-topiramate in μg/ml). The results of those assays are illustrated below in Table 13.

TABLE 13*

| Antibody No. | 9-hydroxy-topiramate | Topiramate | Crossreactivity (Percent) |
|---|---|---|---|
| 662 | 3.1 | 2.6 | 83 |
|  | 6.2 | 5.2 | 83 |
|  | 12.5 | 9.9 | 79 |
|  | 25.0 | 16.3 | 63 |
|  | 50.0 | 26.5 | 53 |
| 787-3 | 4 | 0.51 | 12.8 |
|  | 8 | 0.84 | 10.5 |
|  | 32 | 2.18 | 6.8 |

*In the table, 9-hydroxy-topiramate is the concentration of 9-hydroxy-topiramate in the sample in μg/ml. Topiramate is the observed concentration of topiramate in μg/ml.

This example demonstrates that polyclonal antibody preparations were sufficiently specific for use in a commercial assay when using an immunogen wherein the topiramate analog was derivatized at the sulfamate moiety of topiramate. The antiserum prepared using an immunogen wherein the topiramate analog was derivatizedl at the 9-carbon methyl group provided useful antibodies for immunoassays wherein the amount of the 9-hydroxy-topiramate is relatively small in comparison to the amount of topiramate in the sample.

What is claimed is:

1. A topiramate analog of a formula selected from the group consisting of a compound of the formula

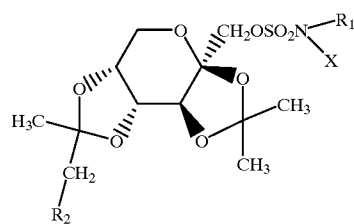

wherein one of $R_1$ and $R_2$ is hydrogen and the other is R-Y, R is a linking group of the formula $(CH_2)_n CO$— wherein n=1–9, and Y is an immunogenic carrier or a detectible label having a terminal amine group with the proviso that when $R_1$ is hydrogen, then X is hydrogen, and with the further proviso that when $R_1$ is R-Y, then X is hydrogen or an alkyl group; and the corresponding 10-carbon $R_2$ derivative.

2. The topiramate analog of claim 1 wherein Y is a carrier.

3. The topiramate analog of claim 1 wherein R-Y is $(CH_2)_n CO$—NH—(carrier), where n=1 to 9.

4. The topiramate analog of claim 2 wherein the carrier is selected from the group consisting of bovine serum albumin and keyhole limpet hemocyanin.

5. The topiramate analog of claim 1 wherein Y is a label.

6. The topiramate analog of claim 5 wherein the label is selected from the group consisting of a fluorochrome, an enzyme, and biotin.

7. The topiramate analog of claim 5 wherein the label is a fluorochrome.

8. The topiramate analog of claim 5 wherein the fluorochrome is fluorescein.

9. The topiramate analog of claim 6 wherein the fluorescein is selected from the group consisting of (2-aminoethyl)-thioureido-fluorescein, fluorescein-thiosemicarbazide, (2-aminoethyl)-ureido-fluorescein, and fluoresceinamine.

10. The topiramate analog of claim 1 wherein the label is a radionuclide.

11. An anti-topiramate antibody.

12. The anti-topiramate antibody of claim 11 wherein the antibody is polyclonal.

13. The anti-topiramate antibody of claim 11 wherein the antibody is monoclonal.

14. The anti-topiramate antibody of claim 11 wherein the antibody reacts with a topiramate analog derivatized at the sulfamate moiety of topiramate.

15. An immunoassay kit for assaying topiramate comprising:
   a. an anti-topiramate antibody; and
   b. a topiramate analog of the formula selected from the group consisting of:

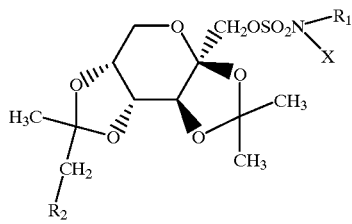

wherein one of $R_1$ and $R_2$ is H and the other is R-Y, R is a linking group of the formula $(CH_2)_nCO$— wherein n=1–9, and Y is a detectable label, when $R_1$ is H, X is H, when $R_1$ is not H, X is H or an alkyl group.

16. The immunoassay kit of claim 15 wherein $R_2$ is R-Y.

17. The immunoassay kit of claim 15 wherein the label is a fluorochrome.

18. A method for assaying topiramate in a sample comprising the steps of:
   (a) combining the sample with a topiramate analog of a formula selected from the group consisting of a compound of the formula

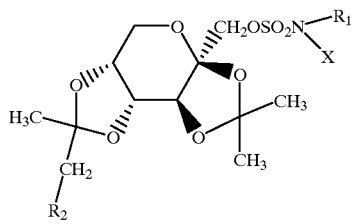

wherein one of $R_1$ and $R_2$ is hydrogen and the other is R-Y, R is a linking group of the formula $(CH_2)_nCO$— wherein n=1–9, and Y is a detectible label having a terminal amine group, with the proviso that when $R_1$ is hydrogen, then X is hydrogen, and with the further proviso that when $R_1$ is R-Y, then X is hydrogen or an alkyl group; the corresponding 10-carbon $R_2$ derivative; and anti-topiramate antibodies;

(b) determining the amount of antibody bound to the topiramate analog as an indication of the amount of topiramate in the sample.

19. The method of claim 18 wherein the topiramate analog is labeled with a fluorochrome.

20. A topiramate analog of the formula:

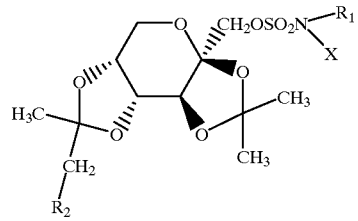

wherein $R_2$ is hydrogen, $R_1$ is R-Y, R is a linking group of the formula $(CH_2)_nCO$— wherein n=1 to 9, and Y is an immunogenic carrier or a detectable label having a terminal amine group; and X is hydrogen or an alkyl group.

21. The topiramate analog of claim 20 wherein Y is a carrier.

22. The topiramate analog of claim 20 wherein R-Y is $(CH_2)_nCO$—NH—(carrier), where n=1–9.

23. The topiramate analog of claim 21 wherein the carrier is selected from the group consisting of bovine serum albumin and keyhole limpet hemocyanin.

24. The topiramate analog of claim 20 wherein Y is a label.

25. The topiramate analog of claim 24 wherein the label is selected from the group consisting of a fluorochrome, an enzyme, and biotin.

26. The topiramate analog of claim 21 wherein the label is a fluorochrome.

27. The topiramate analog of claim 26 wherein the fluorochrome is fluorescein.

28. The topiramate analog of claim 27 wherein the fluorescein is selected from the group consisting of 2-(aminoethyl)-thioureido-fluorescein, fluorescein-thiosemicarbazide, (2-aminoethyl)-ureido-fluorescein, and fluoresceinamine.

29. The topiramate analog of claim 24 wherein the label is radionuclide.

30. An anti-topiramate antibody which reacts with a topiramate analog of claim 20.

31. The antibody of claim 30 wherein the antibody is polyclonal.

32. The antibody of claim 30 wherein the antibody is monoclonal.

33. An immunoassay kit for assaying topiramate comprising:
   (a) an anti-topiramate antibody of claim 30; and
   (b) a topiramate analog of the formula:

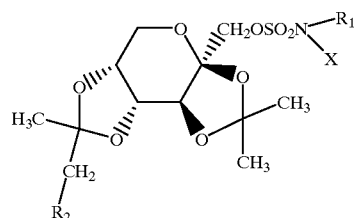

wherein $R_2$ is hydrogen, $R_1$ is R-Y, R is a linking group of the formula $(CH_2)_nCO$— wherein n=1 to 9, and Y is a detectable label having a terminal amine group; and X is hydrogen or an alkyl group.

34. The immunoassay kit of claim 33 wherein R-Y is $(CH_2)_nCO\text{---}NH\text{---}(label)$, where $n=1\text{--}9$.

35. The immunoassay kit of claim 33 wherein the label is a fluorochrome.

36. A method for assaying topiramate in a sample comprising the steps of:

a) combining the sample with anti-topiramate antibodies of claim 30 and a topiramate analog of the formula:

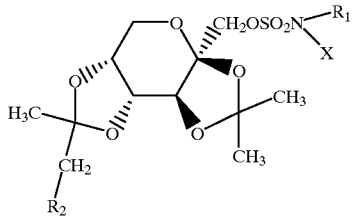

wherein $R_2$ is hydrogen, $R_1$ is R-Y, R is a linking group of the formula $(CH_2)_nCO\text{---}$ wherein $n=1$ to 9, and Y is a detectable label having a terminal amine group; and X is hydrogen or an alkyl group; and b) determining the amount of antibody bound to said topiramate analog as an indication of the amount of topiramate in the sample.

37. The method of claim 36 wherein the topiramate analog is labeled with a fluorochrome.

* * * * *